United States Patent [19]

Bruckenstein et al.

[11] Patent Number: 5,180,968
[45] Date of Patent: Jan. 19, 1993

[54] METHOD AND APPARATUS FOR COMPENSATION OF DOUBLE LAYER CHARGING CURRENT IN ELECTROCHEMICAL CELLS

[75] Inventors: Stanley Bruckenstein, Amherst; Nancy Adinolfe, Pleasant Valley, both of N.Y.

[73] Assignee: Research Foundation of State University of New York, Albany, N.Y.

[21] Appl. No.: 665,607

[22] Filed: Mar. 1, 1991

[51] Int. Cl.⁵ .............................................. G01N 27/00
[52] U.S. Cl. .................................. 324/71.1; 324/425; 204/153.1
[58] Field of Search ...................... 324/425, 439, 71.1; 204/153.1, 153.11, 400, 402

[56] References Cited

U.S. PATENT DOCUMENTS

| | | | |
|---|---|---|---|
| Re. 32,920 | 5/1989 | Matson et al. | 204/153.1 |
| 4,059,406 | 11/1977 | Fleet | 73/61.1 C |
| 4,130,464 | 12/1978 | Kanno et al. | 204/153.1 |
| 4,218,746 | 8/1980 | Koshiishi | 204/153.1 |
| 4,305,039 | 12/1981 | Steuernagel et al. | 324/425 |
| 4,457,808 | 7/1984 | Taylor | 204/153.1 |
| 5,064,516 | 11/1991 | Rupich | 204/153.1 |

Primary Examiner—Jack B. Harvey
Assistant Examiner—Maura K. Regan
Attorney, Agent, or Firm—M. Lukacher; K. Terry

[57] ABSTRACT

A method and apparatus for compensating for charging current at a working electrode of an electrochemical cell. And a method for measuring faradaic current at the working electrode. Includes measuring the current at the working electrode while a time-varying potential difference is applied between the working electrode and a reference electrode. And while the applied potential difference is held constant for a short time and the working electrode current is again measured, where this current is the faradaic current. The faradaic current is then filtered from the total current to determine the charging current thereby compensating for double layer charging current in the cell.

9 Claims, 11 Drawing Sheets

Fig. 1.
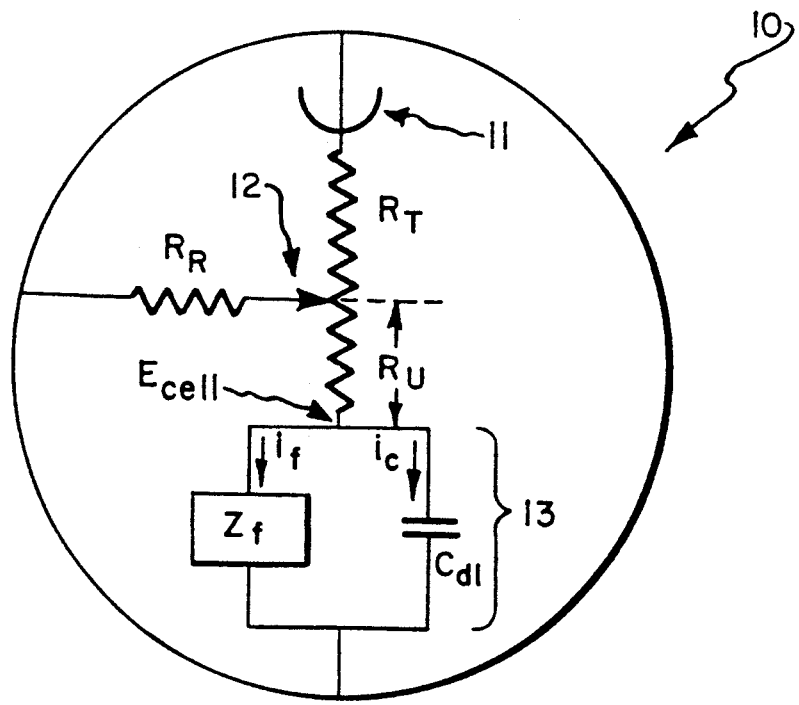
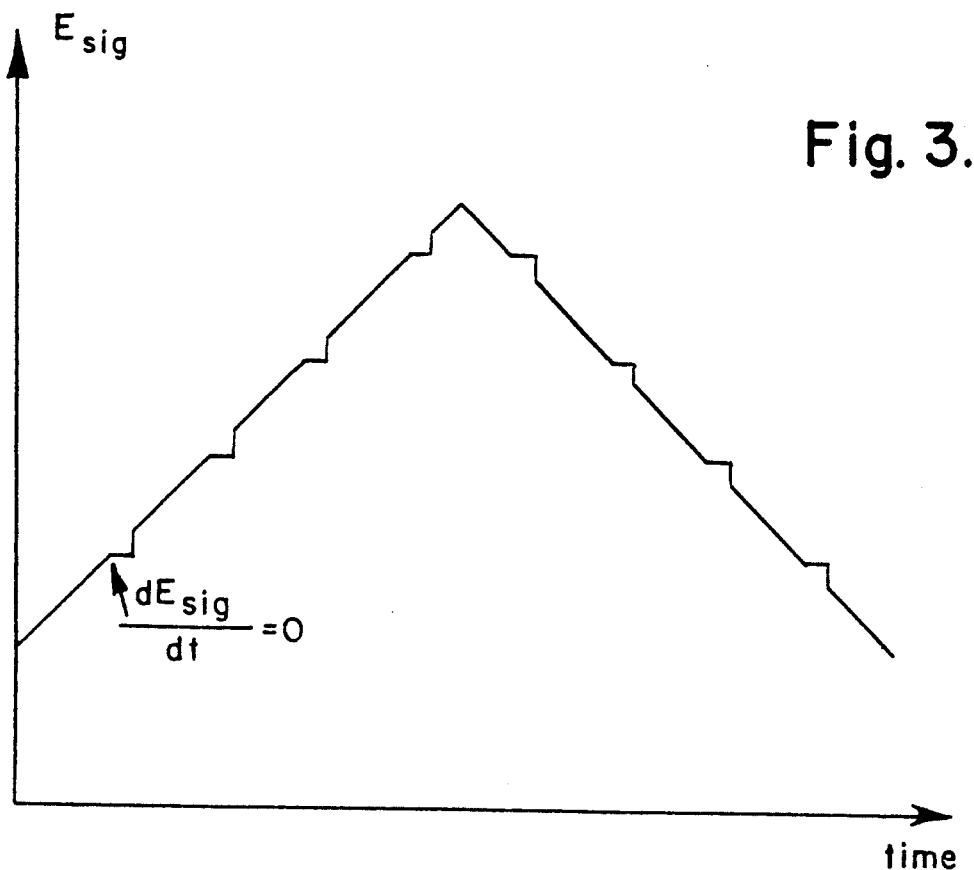
Fig. 3.

Experimental conditions
(for both Figures)

Scan rate = 540 V/s

Upper Limit = +2.5 V
Lower Limit = −2.5 V

Charging current = 0.116 mA

No compensation of ohmic potential drop

METHOD AND APPARATUS FOR COMPENSATION OF DOUBLE LAYER CHARGING CURRENT IN ELECTROCHEMICAL CELLS

The United States Government has certain rights in this invention pursuant to AFOSR Contract 83-0004.

BACKGROUND OF THE INVENTION

The present invention relates to a method and apparatus for compensation of charging current in electrochemical cells, and, more particularly, to real-time double layer current correction using a differential sample/hold technique.

FIG. 1 shows an equivalent circuit of a typical electrochemical cell. The three electrode cell arrangement is now routinely used. Current is furnished to the cell through a counter electrode, and the potential difference between the reference and working electrode is monitored.

There are two types of current in electrochemical cells: 1) faradaic current, and, 2) double layer charging (capacitive) current. Electrochemists are mainly concerned with measuring faradaic current, $i_f$, unless a study of the double-layer capacitance is being done. Faradaic current, $i_f$, is current which passes through the faradaic impedance, $Z_f$, and is due to movement of electrons across the electrode/solution interface. Faradaic currents arising because of redox processes do not affect the analysis.

There is also double layer charging current, $i_c$, in electrochemical cells. At an ideally polarized electrode, the potential across the electrode/solution interface changes and charge flows in an amount required by changes in solute populations adjacent to the electrode solution interface. Charge is accumulated at the electrode/solution interface as the applied potential is varied due to the accumulation or deficiency of electrons at the electrode/solution interface required by changes in the solution ion and dipole populations adjacent to the electrode/solution interface. The separation of charge normal to the electrode/solution interface gives the interface the property of an electrical double-layer and is represented as a double-layer capacitance, $C_{dl}$, in FIG. 1. The accumulation of charge at the electrode solution interface creates charging current in electrochemical cells.

Charge flow is described by Equation 1 as follows:

$$dq_e = A\{C_{dl}(E)\}dE \quad \text{(Eq. 1)}$$

where $dq_e$ is the differential charge flow across the electrode solution interface, accompanying a differential change in potential, A is the electrode area, dE is the differential potential difference across the electrode/solution interface, and, $C_{dl}$ is the differential double-layer capacitance.

The double-layer capacitance is shown as a function of E because the relationship between charge and potential for the electrochemical capacitor is not generally linear.

Current measuring devices measure the sum of faradaic plus charging current. When the charging current becomes a limiting factor in obtaining analytical information, it becomes necessary to compensate or correct for charging current. The problem is to somehow measure and then filter out or isolate the charging current component of the working electrode current to enable an accurate and precise measurement of the faradaic current component.

Many approaches for correcting or compensating for charging current are known in the art. Mathematical methods of charging current correction do not attempt real-time correction for charging current. Mathematical calculations are made after the experiment is performed to remove the unwanted effect of charging current. Known mathematical techniques include curve-fitting methods, Kalman filter, and Cottrell filtration. A disadvantage of curve-fitting techniques is that they usually require a complex, mathematical model for every system studied, and the system must be thoroughly understood. The Cottrell filtration is assumed to contain only charging current as extraneous current; in fact, extraneous currents due to noise, non-linear diffusion and sphericity contributions to the measured current are also present.

Another mathematical method is the derivative method, which plots the derivative of the current with respect to time versus the applied potential. Assuming the differential double-layer capacity is independent of potential, the first derivative of the charging current with respect to time is equal to zero. Hence, there is no contribution of charging current under linear scan voltammetric LSV conditions. The disadvantage of this method is that it is dependent upon the differential double-layer capacitance being constant over the applied potential range. Unfortunately, the double-layer capacitance does change with applied potential.

Other techniques for correcting for charging current are based on response differences between faradaic current and charging current. These techniques do not eliminate charging current, but take into account the presence of charging current and appropriately alter experimentation to yield results which are relatively free from the effects of charging current. These techniques include AC voltammetry and potential step techniques.

Yet another method is the background subtraction method of charging current correction, which subtracts the residual current from the total current. This method subtracts charging current, current caused by impurities in solution, and current due to oxidation or reduction of the electrolyte from the total measured current. A disadvantage of this method is that it usually requires two separate and duplicate experiments, and assumes the charging current in the first experiment is equal to that in the second.

Thus, a need has existed for a real-time instrument correction or compensation of charging current while the experiment is taking place. A need has also existed for a real-time technique which accounts for the charging double-layer capacitance as a function of potential.

SUMMARY OF THE INVENTION

The present invention provides a method and apparatus for compensating for charging current at a working electrode of an electrochemical cell. The invention also includes a method and apparatus for measuring faradaic current in an electrochemical cell which has a time-varying potential applied across its reference and working electrodes. The method for measuring faradaic current broadly includes interrupting the time-varying potential difference and temporarily applying a constant potential difference across the electrodes and measuring a current at the working electrode while the constant potential difference is applied, where the measured current is the faradaic current at the working electrode. The method for compensating for charging current broadly includes first measuring the current at the working electrode while a time-varying potential difference is applied between the working electrode and a reference electrode. This measured current includes both a faradaic and charging current component. Next, the applied potential difference is held constant for a short time and the working electrode current is again measured, where this current is the faradaic current. The faradaic current is then subtracted from the total current to determine the charging current. More specifically, in a preferred embodiment, the method includes the steps of: a. applying a time-varying potential difference between the working electrode and the reference electrode; b. measuring a first current within the working electrode while the time-varying potential difference is being applied, wherein the first current includes a faradaic current component and a charging current component; c. storing a first signal proportional to the first current in a first memory means; d. applying a constant, non-time-varying potential difference between the working electrode and the reference electrode; e. measuring a second current within the working electrode while the constant, non-time-varying potential difference is being applied, wherein the second current is the faradaic current component at an instant when the constant, non-time-varying potential difference is applied; f. determining a second analog or digital signal proportional to the second current; g. determining a difference signal between the first and second analog or digital signals; h. scaling the difference signal in magnitude and sign and summing the difference with the time-varying potential difference to produce a third signal, wherein the third signal is proportional to the charging current component; and, i. repeating steps a. through h. within preselected time intervals. It is to be understood that the term signal is intended to include any analog or digital signal, and in a preferred embodiment, is an analog voltage. Apparatus is also provided for implementing the methods of the invention.

BRIEF DESCRIPTION OF THE DRAWINGS

FIG. 1 is a schematic representation of a typical electrochemical cell.

FIG. 3 is a plot of a modified ramp input signal applied to a potentiostat in a preferred embodiment of the invention.

DETAILED DESCRIPTION OF THE INVENTION

FIG. 1 is a schematic representation of a typical electrochemical cell 10. The three electrode cell includes auxiliary electrode 11 (also sometimes referred to as a counter electrode), reference electrode 12, and working electrode 13. Current supplied to the cell via auxiliary electrode 11 comprises two components, $i_f$, which is the faradaic current component, and $i_c$, which is the charging current component. At the working electrode, $Z_f$ represents the faradaic impedance and $C_{dl}$ represents the double-layer capacitance. The total solution resistance between the auxiliary and working electrodes is designated $R_T$, while the uncompensated resistance between the tip of the reference electrode and the working electrode is designated $R_u$. This uncompensated resistance prevents a three electrode potentiostat from measuring the true potential of the working electrode, $E_{cell}$. The resistance of the reference electrode is designated $R_R$. Finally, $E_{cell}$ is the potential of the cell working electrode across the double-layer capacitance $C_{dl}$.

The charging current, $i_c$, can be shown to be represented by the following equation:

$$i_c = A\{C_{dl}(E_{cell})\}\{dE_{sig}/dt\} \quad \text{(Eq. 2)}$$

where

A is the surface area of the working electrode, $C_{dl}(E_{cell})$ is the double-layer capacitance and, $dE_{sig}/dt$ is the rate of change of the input signal $E_{sig}$ with respect to time, and $E_{sig}$ is assumed to the equal to the potential across the double-layer capacitance, $E_{cell}$.

At a time when the input signal $E_{sig}$ is held constant $dE_{sig}/dt = 0$, and so, according to Equation 2 above, the charging current is also equal to zero. Therefore, by measuring the working electrode current just before and just after the signal potential is held constant and calculating this difference, the faradaic current, $i_f$, can be determined.

Figure 2:
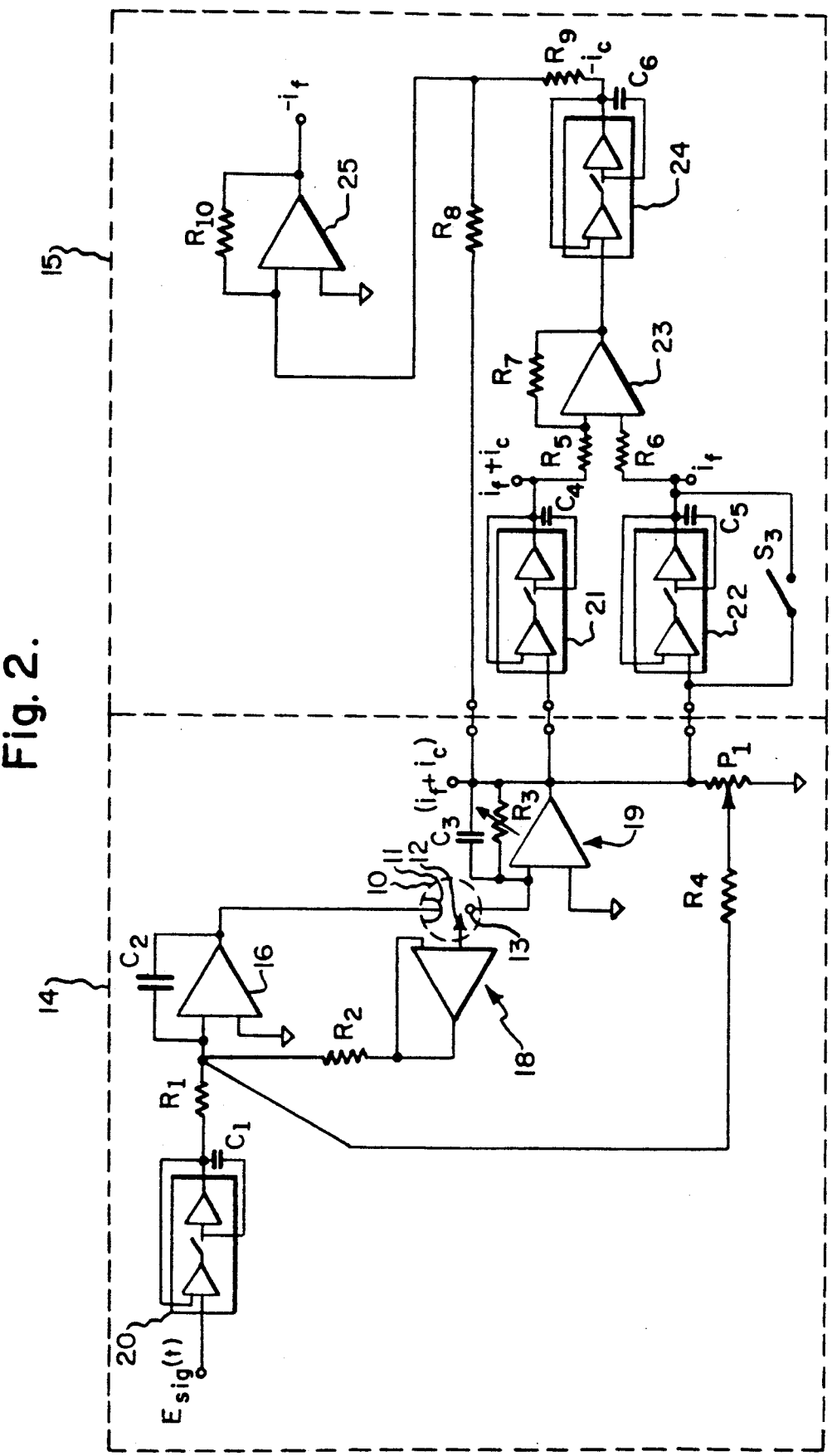
FIG. 2 is a schematic representation of a conventional potentiostat connected to the difference/summing circuit of the present invention.

FIG. 2 illustrates a conventional potentiostat 14 connected to the difference/summing circuit 15 of the present invention. Potentiostat 14 includes electrochemical cell 10, control amplifier 16, voltage follower 18, current follower 19, and sample/hold amplifier 20.

FIG. 3 illustrates the input signal $E_{sig}(t)$ which is applied to potentiostat 14 in a preferred embodiment of the invention. As shown in FIG. 3, the input signal is a modified ramp signal which is periodically interrupted for short time intervals where $E_{sig}$ is held constant (and $dE_{sig}/dt=0$). Although a modified ramp signal is used as the input signal in a preferred embodiment of the invention, it is to be understood that other input signal waveforms are also suitable, as long as the signal is capable of being held constant at predetermined segments of the signal's cycle.

Adverting, once again, to FIG. 2, $E_{sig}(t)$ is applied to sample/hold amplifier 20 of potentiostat 14. Current follower 19 senses and measures the current in working electrode 13 (as shown in FIG. 1), which current comprises faradaic current component, $i_f$, and charging current component, $i_c$. The working electrode current measurement is communicated to difference/summing circuit 15 (as a voltage signal which is proportional to the working current) which filters or subtracts out the charging current component and determines the faradaic component, $i_f$.

The sign of the charging current depends upon scan direction. It changes sign when scan direction is reversed. Circuit performance is not affected by the change in sign of the charging current, and yields the same result for the faradaic current at the output of the summing circuit. Before the scanning potential is held constant, the output of the potentiostat's current follower 19 is a voltage which is directly related to the sum of the faradaic and charging currents, i.e.:

$$i_{before} = i_f + i_c \qquad (Eq. 3)$$

A voltage equivalent to the total current ($i_f+i_c$) is sampled and held at the output of sample/hold amplifier 21 (shown in FIG. 2). Note that $i_c$ represents the algebraic value of the charging current (magnitude and sign).

Immediately after the scanning potential is held constant, the charging current is equal to zero according to Equation 1. Therefore, the output of current follower 19 is free from the charging current component and:

$$i_{after} = i_f \qquad (Eq. 4)$$

A voltage equivalent to the faradaic current, $i_f$, is sampled and held at the output of sample/hold amplifier 22. The digital difference circuit measures the difference between the two currents in Equations 3 and 4. Therefore, a continuously updated measurement of the charging current (with a sign inversion) yields:

$$i_{after} - i_{before} = -i_c \qquad (Eq. 5)$$

during the forward scan (and $+i_c$ during the reverse scan). A voltage equivalent to the charging current is sampled and held constant until the next cycle at the output of sample/hold amplifier 24.

Summing amplifier 25 measures the sum of the output of current follower 19 (Equation 3) plus the output of the digital difference circuit (Equation 5) and provides an output voltage which is proportional to:

$$-\{(i_f+i_c)+(-i_c)\} = -i_f \qquad (Eq. 6)$$

The output of summing amplifier 25, therefore, is a voltage which is directly related to the faradaic current and correction of charging current is accomplished. The sign inversion occurs due to the manner of inputting voltages into the inverting input of the summing amplifier. During the reverse scan, the output of the summing amplifier will also be proportional to $-i_f$.

Experimental Results

Figure 4:
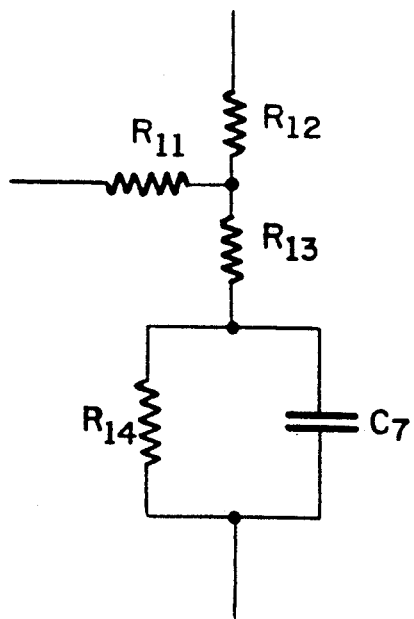
FIG. 4 is a schematic representation of a dummy cell used to simulate electrochemical cells in testing the present invention.

Six different electrochemical cells were used to test the charging current compensation apparatus of the present invention. Table 1 summarizes the characteristics and values of the components used in the dummy cell shown in FIG. 4.

TABLE 1

| Dummy Cell # | Dummy Cell Components | | | | |
|---|---|---|---|---|---|
| | $R_{11}$ | $R_{12}$ | $R_{13}$ | $R_{14}$ | $C_7$ |
| 1) | 25 kΩ | 300 Ω | 74.5 Ω | 10 kΩ | 0.213 μF |
| 2) | 25 kΩ | 300 Ω | 74.5 Ω | ∞ | 0.213 μF |
| 3) | 25 kΩ | 300 Ω | 220.3 Ω | 10 kΩ | 0.213 μF |
| 4) | 25 kΩ | 300 Ω | 220.3 Ω | ∞ | 0.213 μF |
| 5) | 25 kΩ | 330 Ω | 4.7 kΩ | ∞ | 0.213 μF |
| 6) | 10 kΩ | 50 Ω | 50 kΩ | 390 kΩ | 3.5 μF |

The "faradaic resistor", $R_{14}$, was a model faradaic impedance in our dummy cell. However, it should be remembered that $Z_F$ introduces a phase shift at the double layer capacitance in electrochemical cells which is not present in the dummy cell.

In a preferred embodiment, the input ramping potential was produced by a Global Specialties, 2005 5 MHz Function Generator for scans rates of 540 V/s and 54 V/s. For the slower scan rate of 0.429 V/s used in Dummy Cell #6, the input ramping potential was provided by an analog function generator substantially identical to that disclosed in Untereker, D. F., et al., *An Analog Function Generator for Voltammetric Applications*, Chemical Instrumentation, 6(3), pp. 259-266 (1975), and incorporated herein by reference. A Hewlett Packard, Model 7046B x-y recorder was used for an analog output display.

The following five electrochemical systems were studied:

| System | RDE, Metal | Area |
|---|---|---|
| 1) 0.610mM AgNO$_3$/0.2M H$_2$SO$_4$ | Au | 0.07116 cm$^2$ |
| 2) 0.6mM K$_3$Fe(CN)$_6$/0.5M KCl | Pt | 0.07448 cm$^2$ |
| 3) 0.344mM Hg(NO$_3$)$_2$/1M HNO$_3$ | Pt | 0.07448 cm$^2$ |
| 4) 0.687mM Hg(NO$_3$)$_2$/1M HNO$_3$ | Pt | 0.07448 cm$^2$ |
| 5) 0.5mM KI/0.2M H$_2$SO$_4$ | Pt | 0.07448 cm$^2$ |

(RDE is a rotating disk electrode.)

The auxiliary electrode was a platinum coiled wire in a compartment separated from the electrochemical cell by a glass frit. Potentials were measured versus the saturated calomel electrode, SCE. The cells were de-aerated with N$_2$ and various rotation rates were used.

Disk electrodes were buffed with a mixture of 0.05 micron alumina/water on a polishing cloth (available from Buehler Ltd.) to remove contaminants and rinsed with distilled water immediately prior to use. The Luggin probe was positioned directly under the disk electrode at a distance of about a few millimeters.

Reagent grade chemicals were used with filtered "millipore" water prepared from a Milli-Q Plus System.

Instrumentation

The instrumentation section is divided into three sections because the voltage scan rates differed by three orders of magnitude and circuit components changed according to the scan rate. The scan rates used were, 1) 540 V/s,
2) 54 V/s,
3) 1 V/s and less.

All three magnitudes of scan rates were used with dummy cells. However, electrochemical cells using the rotating disk electrode were confined to lower scan rates less than 1 V/s. These scan rates were selected in order to use an x-y recorder and also to obtain steady-state, convective-diffusion controlled voltammograms. Nonsteady state effects occur when the scan rate is too fast for a given rotation speed.

Two factors must be considered when the circuit timing is adjusted: 1) the fraction of time the ramp potential is held constant (the time the ramp potential is constant divided by the time the voltage scans before it is again held constant,) and 2) the difference between the ramp potential immediately before it is held constant minus the ramp potential immediately after ramping resumes. This was determined by multiplying the scan rate by the time the ramp potential was held constant. The amount of time the ramp potential remained constant could be increased for slower scan rates. Therefore, the fraction of time the ramp potential was constant was the same for each scan rate.

Instrumentation For Scan Rate Of 540 V/s

The potentiostat circuit was shown in FIG. 2 with the addition of sample/hold amplifier 20 and positive feedback of iR compensation from potentiometer $P_1$ at the output of the current follower 19. FIG. 2 omits details of current booster amplifiers and chopper stabilizer amplifiers. Sample/hold amplifier 20 provides the appropriate waveform to the electrochemical cell. Positive feedback from current follower 19 establishes compensation of the solution resistance. The amount of positive feedback was calculated for each individual dummy cell tested.

It was convenient to stabilize the sample/holds to avoid trimming the digital difference circuit. The circuit details of chopper stabilized sample/holds are shown in FIG. 5.

The chopper stabilizer functions to maintain the difference in voltage between the inverting and noninverting inputs (termed an offset voltage) of the sample/hold equal to zero. Whenever there is an offset voltage, it is detected at the noninverting input of the chopper stabilizer. The chopper compares its inverting and noninverting voltages in a nulling amplifier. The nulling amplifier continuously adjusts its output voltage until the offset voltage is zero. The results of chopper stabilization of the sample/holds is shown in Table 2.

TABLE 2

Figure 5:
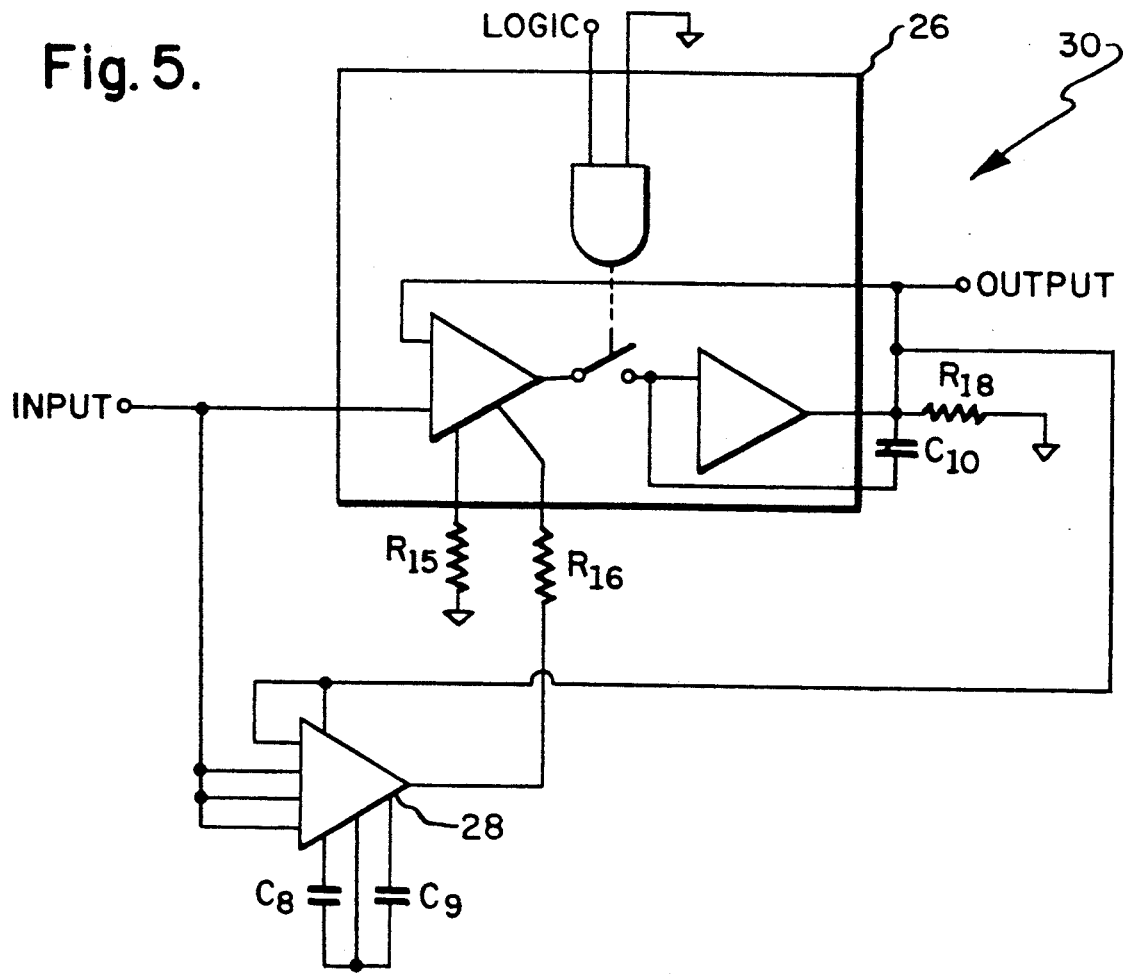
FIG. 5 is a schematic representation of a circuit used to chopper stabilize the sample/holds of the present invention.

Input/Output of Chopper Stabilized Sample/Hold Shown in FIG. 5
Input/Output (Volts)

| |
|---|
| 7.5004/7.5004 |
| −7.5009/−7.5009 |
| 0.000002/0.000012 |
| −0.75057/−0.75058 |
| 0.75128/0.75130 |

Figure 6:
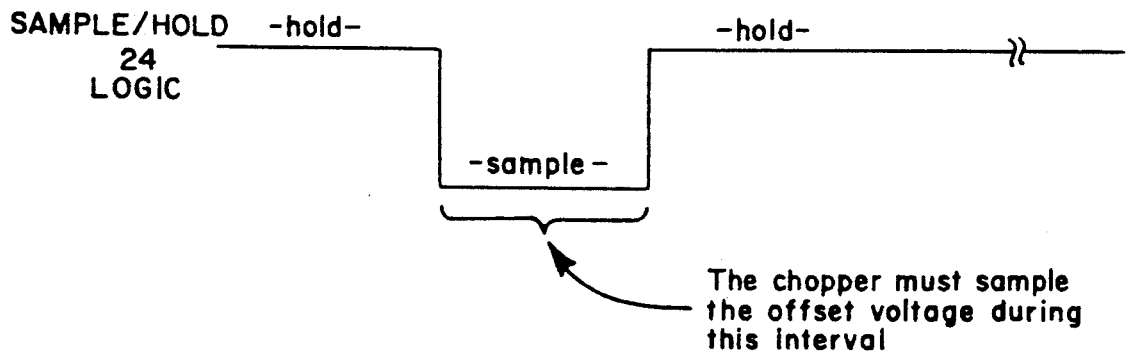
FIG. 6 illustrates the logic of a sample/hold amplifier of the invention.

It proved to be very difficult to chopper stabilize sample/hold amplifier 24. The chopper frequency of the MAX421 is 435 Hz. In other words, every 2.3 ms the chopper stabilizer samples the input signal from difference amplifier 23. However, sample/hold amplifier 24 sampled the output of difference amplifier 23 for approximately 20 μs every millisecond, and, therefore, there is only a very short duration of about 20 μs approximately every millisecond the chopper can sample. If the chopper samples at any other time, it will not obtain the right offset voltage. FIG. 6 demonstrates this point.

Trimming of the instrumentation to correct for charging current was done when the dummy cell was in the circuit. The voltage follower input was grounded and trimmed using a potentiometer until its output was 0.00 mV. The two input terminals to the difference amplifier were connected together, and the difference amplifier output potential was verified to be zero. Finally, the third sample/hold 22 was trimmed using a potentiometer with zero input. Sample/holds 20 and 21 did not need to be trimmed because they were chopper stabilized.

Timing Circuitry For Scan Rate Of 540 V/s

Figure 7:
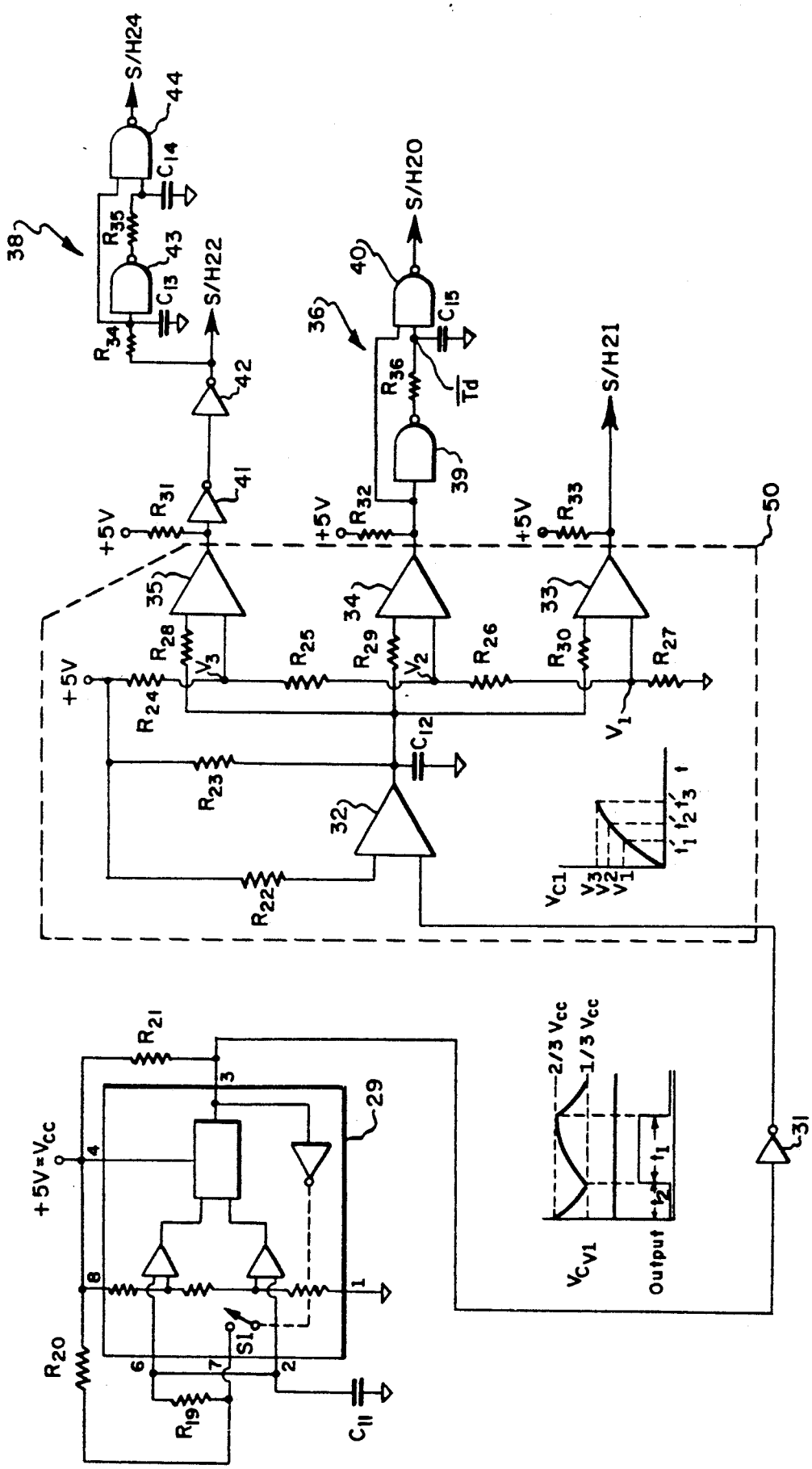
FIG. 7 is a schematic representation of a timing circuit used in a preferred embodiment of the invention.

The timing circuit is shown in FIG. 7. All circuit components are clocked from 555-timer 29 configured as an astable multivibrator. A logic of 1 (true) is a high voltage (2.4–4.5 volts), and a logic of 0 (false) is a low voltage (0.0–0.4 volts). When the power is turned on, the output at pin 3 is high. The switch $S_1$ is open; therefore, the timing capacitor $C_{11}$ is uncharged. The timing capacitor will charge to an upper threshold voltage $\frac{2}{3}V_{cc}$ large enough to cause the 555-timer to change state. The output now goes low. The switch closes and the capacitor $C_{11}$ discharges through resistor $R_{19}$. When the voltage across the timing capacitor reaches the lower threshold $\frac{1}{3}V_{cc}$, the circuit will revert back to its high output state. The circuit oscillates between the two upper and lower threshold voltages as shown in FIG. 7 and changes state accordingly. The low-to-high pulse of the multi-vibrator triggers a time-delay generator.

Time-delay generator 50 shown in FIG. 7 includes four comparators 32, 33, 34 and 35 (LM393 or equivalent). Three successive pulses with different time delays are produced in response to the input gating signal. The comparators go from a high-to-low state at the same time as the input signal goes from high-to-low. The RC time constant at the output of comparator 32 provides a slowly rising voltage with time at the noninverting input of the remaining comparators. A voltage divider network provides reference voltage $V_1$, $V_2$ and $V_3$ at the inverting input of the comparators. When the reference voltage is equal to the voltage at the noninverting input, the comparator changes state. The time at which the pulses occur can be varied by changing the RC time constant and the resistors in the voltage divider network. The first pulse generated by comparator 33 is directly connected to sample/hold 21. The second pulse of the time-delay generator at the output of comparator 34 triggers RC delay monostable 36.

RC delay monostable 36 includes cross-coupled NAND gates 39 and 40 (CD74HCT00E or equivalent). The output of the NAND gates is high when the trigger is low at the beginning of the trigger pulse. The output of the NAND gates will immediately go to low when the trigger pulse goes high. The output of NAND gate 39 becomes low at this time also. The voltage at $T_d$ decreases with time constant $R_{36}C_{15}$ and crosses the high-to-low threshold for gate 40. At this time the low $T_d$ brings gate 40 output high. The pulse duration of the cross-coupled NAND gates is approximately equal to the time constant $R_{36}C_{15}$. RC delay monostable 36 provides logic levels to the switches.

The third pulse of the time-delay generator (from comparator 35) is connected to two inverters 41 and 42 with Schmitt triggers (7414) in series. The output of the inverters have two connections. One connection is to sample/hold 22. The other connection is used to trigger RC delay monostable 38 which has an additional delay at its input. This second monostable provides the logic necessary to control sample/hold 24. Inverters 41 and 42 are necessary to avoid loading of the time-delay generator and are able to drive the input RC delay of monostable 38. If the inverters are not used, the monostable may draw too much current from the comparator and the comparator may not reach +5 V at its output.

Hex inverters with Schmitt triggers (7414 or equivalent) were used when necessary to provide the correct logic to the comparators, switches and sample/holds. The values of capacitors and resistors can be seen in Table 3.

TABLE 3

Component Values Used For Logic Control
(Scan Rates of 540 V/s)

| Astable Multivibrator 29 (555-timer) | Time Delay Generator 50 |
|---|---|
| $R_{20}$ = 13.272 kΩ | $R_{27}$ = 100 kΩ |
| $R_{19}$ = 1.9363 kΩ | $R_{26}$ = 10 kΩ |
| $R_{21}$ = 10 kΩ | |
| $C_{11}$ = 0.1038 μF | $R_{25}$ = 200 kΩ |
| | $R_{24}$ = 389.9 kΩ |
| | $R_{23}$ = 33 kΩ |
| | $C_{12}$ = 3.09 nF |
| | $R_{31}$ = 3 kΩ |
| | $R_{32}$ = 3 kΩ |
| | $R_{28}$ = 10 kΩ |
| | $R_{29}$ = 10 kΩ |
| | $R_{30}$ = 10 kΩ |
| RC Delay Monostable 36 | |
| $R_{36}$ = 3.3 kΩ | |
| $C_{15}$ = 40.08 nF | |
| | RC Delay Monostable 38 |
| $R_{35}$ = 3.3 kΩ | $R_{34}$ = 30 kΩ |
| $C_{14}$ = 12.52 nF | $C_{13}$ = 636 pF |

Figure 8:
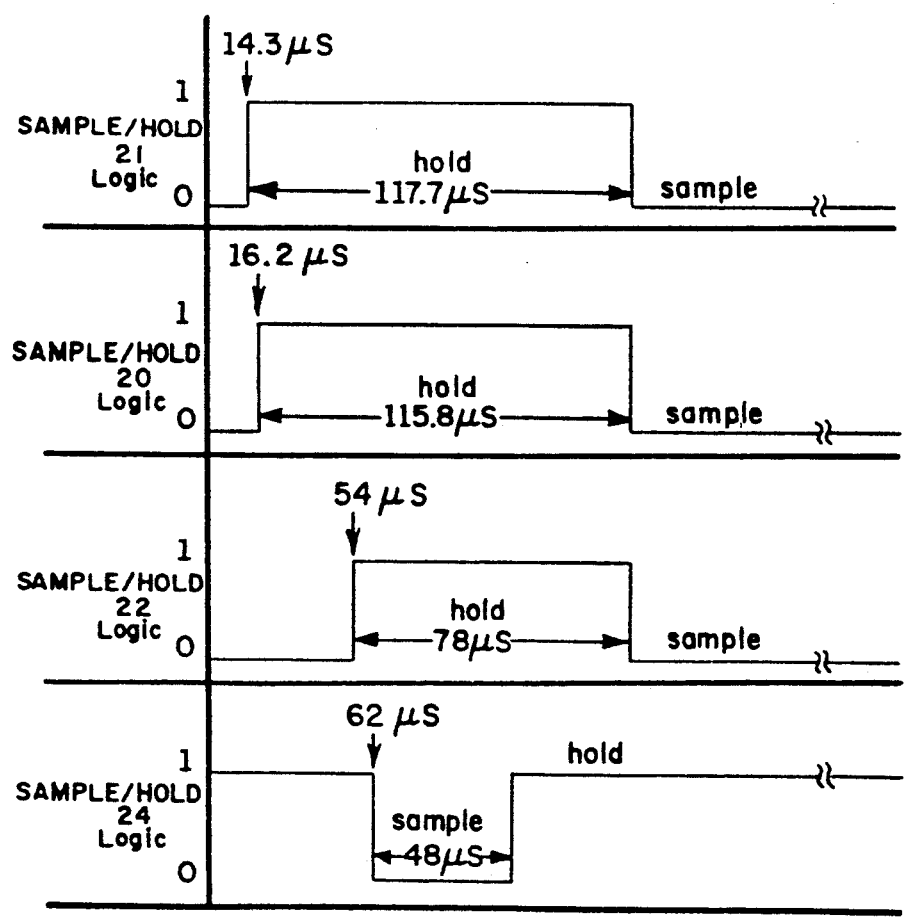
FIG. 8 illustrates a timing diagram for fast scan rates (540 V/s) used in testing the invention.

The clock diagram shown in FIG. 8 shows the logic timing that was used for fast scan rates. A logic 1 (true) is a high voltage (2.4–4.5 V), and a logic 0 (false) is a low voltage (0.0–0.4 V).

The 555-timer generates a high state for 132 μs and a low state for 1,048 μs. Therefore, one duty cycle consists of a pulse of 132 μs emitted every 1,180 μs.

The first pulse of the time-delay generator has a delay of 14.3 μs. Sample/hold 21 is adjusted to hold for 117.7 μs and sample for 1,048 μs every 1,180 μs. The second pulse of the time-delay generator has a delay of 16.2 μs and the RC time constant of RC Delay Monostable 36 is 132 μs. Therefore, sample/hold 20 is adjusted to hold for 115.8 μs and sample for 1,048 μs every 1,180 μs. The third pulse of the time-delay generator has a delay of 54 μs; therefore, sample/hold 22 is adjusted to hold for 78 μs and sample for 1,048 μs every 1,180 μs. The additional delay of RC Delay Monostable 38 produces a delay of 8 μs. The monostable will produce a low pulse for 48 μs and a high pulse very 1,240 μs. Sample/hold 25 samples for 48 μs and holds for 1,130 μs.

The percentage of time sample/hold 20 is held during one duty cycle is:

$$(117.7 \ \mu s/1,180 \ \mu s) \times 100 = 9.97\% \qquad (Eq. 7)$$

The change in ramp potential from the time the scan is held constant until the time the scan resumes is:

$$(117.7 \ \mu s) \times (540 \ V/s) = 63.6 \ mV \qquad (Eq. 8)$$

Instrumentation For Scan Rates of 54 V/s

The instrumentation used for slower scan rates (e.g., 54 V/s) is the same as that used for 540 V/s (as shown in FIG. 2), except that sample/hold 22 is removed (short circuited). Adverting to FIG. 2, slower scan rates may be achieved by decreasing $E_{sig(t)}$. $E_{sig(t)}$ can be obtained by using an appropriate triangular wave generator. The potentiostat is the same as that used for 540 V/s scan rates. It was found that removing the sample/hold produced greater stability when slower scan rates (54 V/s and less) were used. The ramping potential was held constant on time scales of the order of milliseconds. This allowed enough time for sample/hold 24 to acquire the correct difference potential.

The trimming procedure for the scan rate of 54 V/s is the same as that of 540 V/s.

Timing Circuitry For Scan Rate Of 54 V/s

The timing circuitry for scanning at 54 V/s is the same as that for 540 V/s as shown in FIG. 7, except RC Delay Monostable 36 is removed from the circuit. Therefore, the logic to enable sample/hold 20 is directly connected to the output of the second pulse emitted from the time-delay generator. Table 4 shows the resistor and capacitor values used in the timing circuitry.

TABLE 4

Component Values Used for Logic Control
(Scan Rates of 54 V/s)

| Astable Multivibrator 29 (555-timer) | Time Delay Generator 50 |
|---|---|
| $R_{20}$ = 27.32 kΩ | $R_{27}$ = 100 kΩ |
| $R_{19}$ = 3.2723 kΩ | $R_{26}$ = 10 kΩ |
| $R_{21}$ = 10 kΩ | |
| $C_{11}$ = 1.027 μF | $R_{25}$ = 200 kΩ |
| | $R_{24}$ = 389.9 kΩ |
| | $R_{23}$ = 33 kΩ |
| | $C_{12}$ = 50 nF |
| | $R_{31}$ = 3 kΩ |
| | $R_{32}$ = 3 kΩ |
| | $R_{28}$ = 10 kΩ |
| | $R_{29}$ = 10 kΩ |
| | $R_{30}$ = 10 kΩ |
| RC Delay Monostable 36 | |
| Nothing is placed in NAND gates | |
| Signal for sample/hold 20 was directly from Time Delay Generator 50 | |
| RC Delay Monostable 38 | |
| $R_{35}$ = 100.05 kΩ | $R_{34}$ = 33 kΩ |
| $C_{14}$ = 9.08 nF | $C_{13}$ = 1.879 pF |

Figure 9:
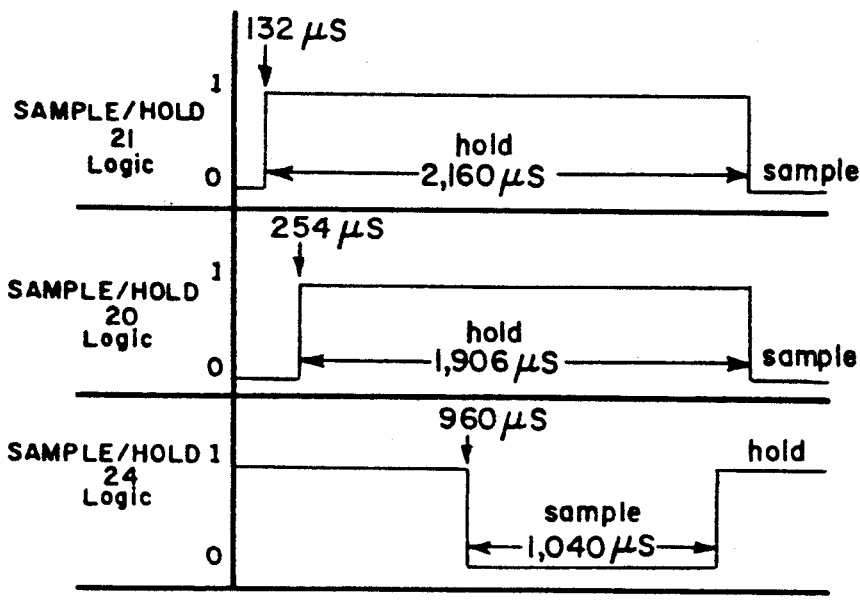
FIG. 9 illustrates a timing diagram for scan rates of 54 V/s used in testing the invention.

The clock diagram shown in FIG. 9 shows the logic timing that was used for scan rates of 54 V/s. A logic 1 (true) is a high voltage (2.4–4.5 V), and a logic 0 (false) is a low voltage (0.0–0.4 V).

The 555-timer generates a high state for 2.16 ms and a low state for 19.84 ms. Therefore, one duty cycle consists of a pulse of 2.16 ms emitted every 22.00 ms.

The first pulse of the time-delay generator has a delay of 0.132 ms. Sample/hold 21 is adjusted to hold for 2.16 and sample for 19.84 ms every 22.00 ms. The second pulse of the time-delay generator has a delay of 0.254 ms. Therefore sample/hold 20 is adjusted to hold for 1.906 ms and sample for 20.094 ms every 22.00 ms. The additional delay of RC Delay Monostable 38 plus the delay of the third pulse of the time-delay generator produces a total delay of 0.960 ms. The monostable will produce a low pulse for 1.04 ms and a high pulse every 23.00 ms. Sample/hold 24 samples for 1.04 ms and holds for 21.00 ms.

The percentage of time sample/hold 20 is held during one duty cycle is:

$$(2.16\ ms/22.00\ ms) \times 100 = 9.82\% \quad \text{(Eq. 9)}$$

The change in ramp potential from the time the scan is held constant until the time the scan resumes is:

$$(2.16\ ms) \times (54\ V/s) = 116.64\ mV \quad \text{(Eq. 10)}$$

Instrumentation For Scan Rates Less Than 1 V/s

Figure 10:
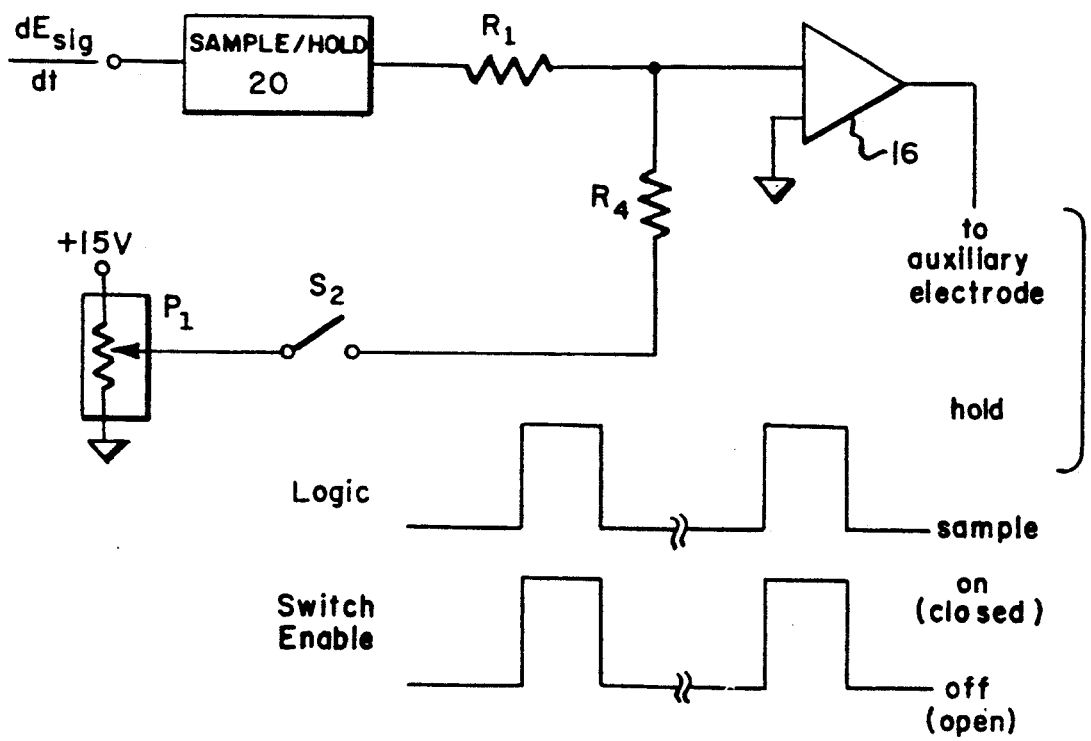
FIG. 10 illustrates a modified control amplifier input signal used in testing the invention at scan rates of less than 1 V/s.

The potentiostat is identical to that previously described in FIG. 2, except with the addition of offset switch $S_2$ at the summing point of control amplifier 16 shown in FIG. 10. The switch was necessary for low scan rates due to a 3 mV sample-to-hold offset potential which occurred when sample/hold 20 was in the hold mode. This sample-to-hold offset produced an offset in the i-E curves. The curves which were recorded without sample/hold 20 in the circuit did not trace over the curves with sample/hold 20 in the circuit. The switch was closed (on) when sample/hold 20 was in the hold mode and open (off) when sample/hold 20 was in the sample mode. Therefore, the switch injected a 3 mV potential from potentiometer $P_1$ while sample/hold 20 was in the hold mode to eliminate the sample-to-hold offset potential of sample/hold 20.

Trimming of the instrumentation to correct for charging current was done when the test cell was in the circuit. The procedures described for higher scan rates were used to trim the charging current correction circuit.

The additional switch $S_2$ at the summing point of the control amplifier permitted trimming the offset. The potentiometer shown in FIG. 10 was adjusted until the offset potential as observed on an oscilloscope was no longer present when switch $S_2$ was closed.

When electrochemical cells were tested, several i-E curves were recorded. One was without the charging current compensator in the circuit, and the other was with the compensator in the circuit. The two curves traced over each other which indicated sample/hold 20 was not creating any offset.

Timing Circuitry For Scan Rates Less Than 1 V/s

Figure 11:
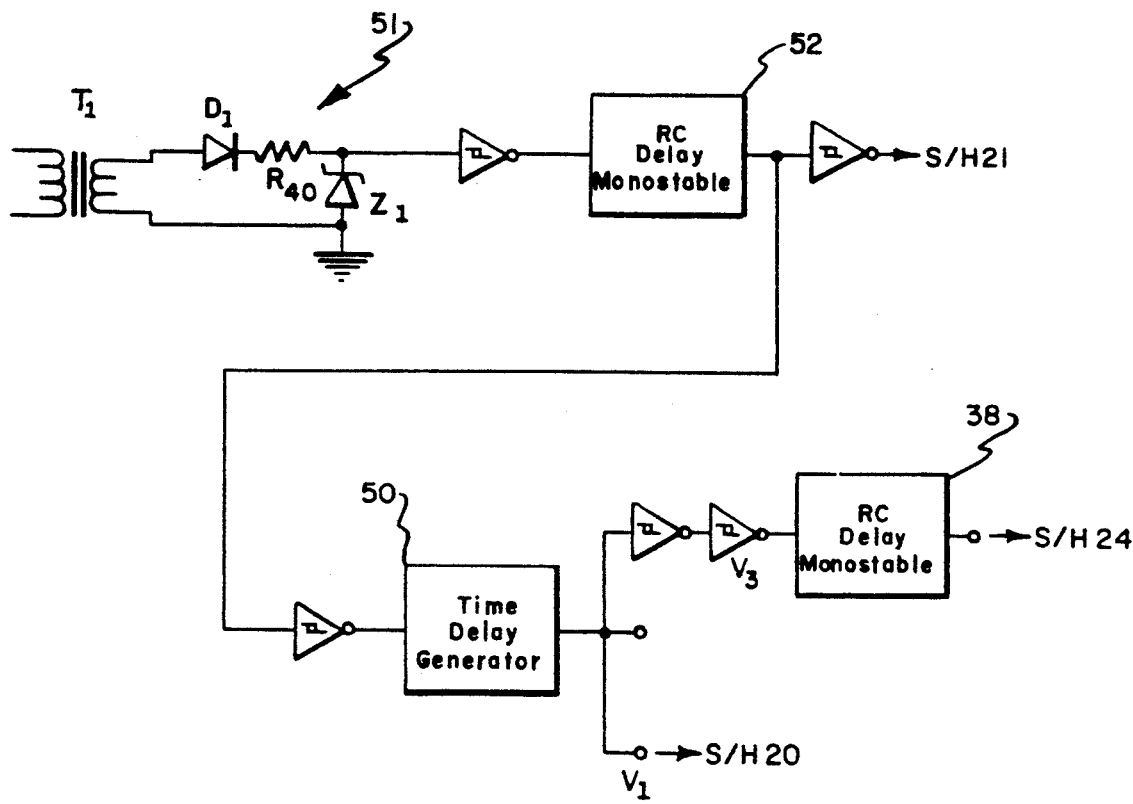
FIG. 11 illustrates modified timing circuitry used in testing the invention at scan rates of less than 1 V/s.

The timing circuitry for these scan rates required an alternative main clock. The 555-timer shown previously in FIG. 7 was replaced by half-wave rectifier circuit 51 and RC delay monostable 52 as shown in FIG. 11. This clocked the delay circuitry at the same point on the ac line and eliminated the effect of ac line noise.

Transformer $T_1$ of rectifier circuit 51 transformed the 100 V, ac power supply to a 10 $V_{rms}$ ac power supply. The rectifier diode $D_1$ (1N5310 or equivalent) was forward biased and had the 10 $V_{rms}$ ac sinusoidal signal (14.1 V peak potential) applied to its anode. Diode $D_1$ conducts current on the positive side of the ac signal. The diode is reversed biased and nonconducting on the negative side of the ac signal. Therefore, the diode transformed the ac sinusoidal wave to a waveform which produced only the positive component of the 10 $V_{rms}$ ac wave. The purpose of Zener diode $Z_1$ (1N749 or equivalent) was to produce a 60 Hz square wave that conducted only positive currents. When the current going into the cathode of the Zener diode is greater than the breakdown reverse bias current, the voltage across the Zener diode will be regulated at the Zener voltage $V_Z$ (4.3 V). The current through resistor $R_{40}$ must be large enough to reach the sum of the reverse bias current of the Zener diode plus supply enough current to the load. Also, resistor $R_{40}$ must be large enough so the power dissipation rating for the Zener diode is not exceeded. When the applied voltage is greater than the breakdown voltage $V_Z$, the voltage across resistor $R_{40}$ is about 9 V. The power dissipation P is:

$$P = V^2/R_{40} \quad \text{(Eq. 11)}$$

and, therefore, $$\begin{aligned} R_{40} &= V^2/P \\ &= (9\ V^2)/0.25\ W \\ &= 324\ \Omega \end{aligned} \quad \text{(Eq. 12)}$$

This resistance value is also large enough for the sum of Zener breakdown current plus current to the load (39 mA), i.e., $$4.3\ V/39\ mA = 110\ \Omega$$

RC delay Monostable 52 was triggered by rectifier circuit 51. The monostable then supplied Time-Delay Generator 50 with the correct logic. The resistor and capacitor values of the timing circuitry are shown in Table 5.

TABLE 5

Component Values Used For Logic Control
(For Scan Rates of 1 V/s or Less)

| RC Delay Monostable 52 | Time Delay Generator 50 |
|---|---|
| R = 75 kΩ | $R_{27}$ = 100 kΩ |
| C = 1.027 μF | $R_{26}$ = 500 kΩ |
| | $R_{25}$ = 700 kΩ |
| | $R_{24}$ = 389.9 kΩ |
| | $R_{23}$ = 33 kΩ |
| | $C_{12}$ = 50 nF |
| | $R_{31}$ = 3 kΩ |
| | $R_{32}$ = 3 kΩ |
| | $R_{28}$ = 10 kΩ |
| | $R_{29}$ = 10 kΩ |
| | $R_{30}$ = 10 kΩ |
| RC Delay Monostable 36 | |
| Nothing is placed in NAND gates | |
| Signal for sample/hold 20 was directly from Time Delay Generator 50 | |
| RC Delay Monostable 38 | |
| $R_{35}$ = 143 kΩ | $R_{34}$ = 150 kΩ |
| $C_{14}$ = 3.01 nF | $C_{13}$ = 8.78 nF |

Figure 12:
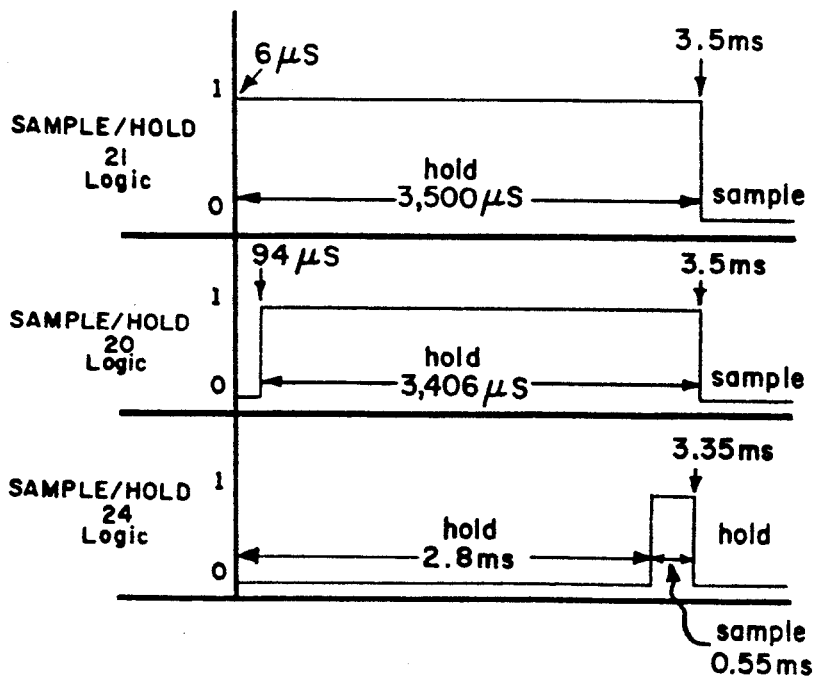
FIG. 12 illustrates a timing diagram for scan rates less than 1 V/s used in testing the invention.

The clock diagram shown in FIG. 12 shows the logic timing that was used for scan rates less than 1 V/s. A logic 1 (true) is a high voltage (2.4–4.5 V), and a logic 0 (false) is a low voltage (0.0–0.4 V).

The Schmitt trigger at the output of RC Delay Monostable 52 generates a high state for 3.49 ms and a low state for 12.30 ms. Therefore, one duty cycle consists of a 3.49 ms pulse emitted every 15.80 ms.

Sample/hold 21 logic is taken directly from the Schmitt trigger of RC Delay Monostable 52 and the external trigger of the oscilloscope is taken from the rectifier circuit. This generates a 6 μs delay. Therefore, sample/hold 21 is adjusted to hold for 3.49 ms and sample for 12.30 ms every 15.80 ms. The first pulse of the time delay generator has a delay of 0.094 ms. Therefore, sample/hold 20 is adjusted to hold for 3.406 ms and sample for 12.39 ms every 15.89 ms. The additional delay of RC Delay Monostable 38 plus the delay of the third pulse of the time-delay generator produces a total delay of 2.80 ms. The monostable will produce a low pulse for 0.55 ms and a high pulse every 18.60 ms. Sample/hold 24 samples for 0.55 ms and holds for 15.25 ms.

The percentage of time sample/hold 20 is held during one duty cycle is:

$$(3.40 \text{ ms}/15.89 \text{ ms}) \times 100 = 21.40\% \quad \text{(Eq. 13)}$$

The change in ramp potential from the time the scan is held constant until the time the scan resumes is:

$$(3.40 \text{ ms}) \times (1 \text{ V/s}) = 3.4 \text{ mV} \quad \text{(Eq. 14)}$$

Values of Stabilizing Capacitors

Stabilizing capacitors were placed across the feedback loops of the control amplifier and current follower. The capacitors are shown in FIG. 2. Table 6 shows the values of the capacitors and the corresponding scan rate.

TABLE 6

Values of Stabilizing Capacitors

| Experimental Condition | Capacitor Across Control Amplifier | Capacitor Across Current Follower |
|---|---|---|
| 540 V/s | 300 pF | 503 pf |
| 54.3 V/s | 3 nF | — |
| 1 V/s and less | | |
| (dummy cell) | 200 pF | 11 nf |
| (electrochemical) | — | 20 nF |

There was also a 2 $\mu$F capacitor across the feedback loop of the summing amplifier when the electrochemical cells were tested.

Results and Discussion

Dummy Cell Experiments

Figure 13:
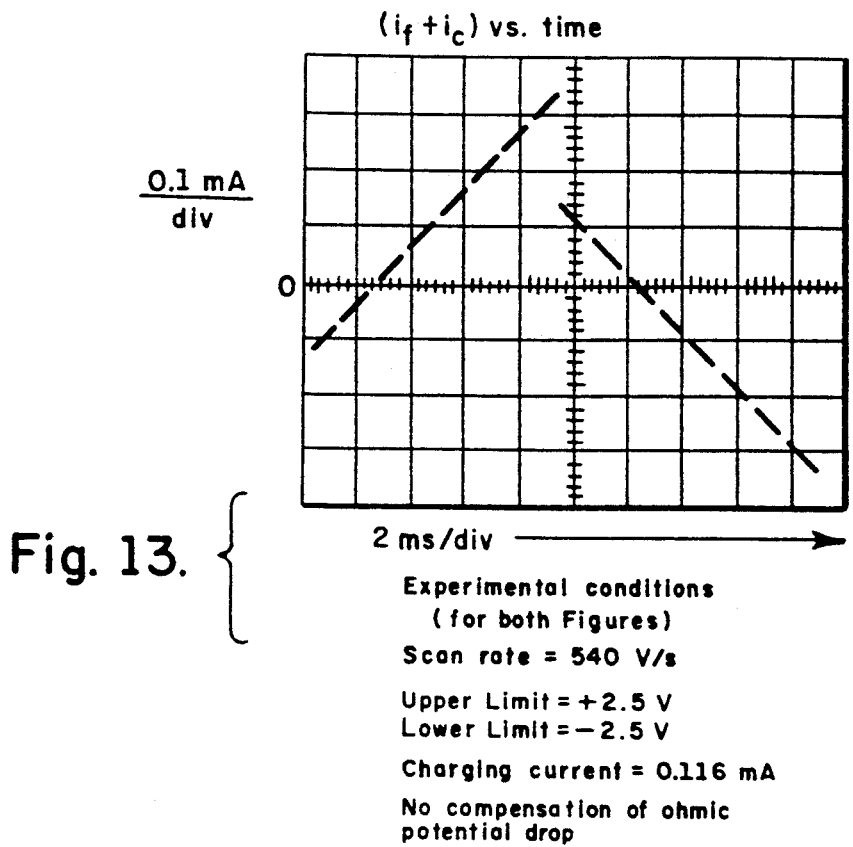
FIG. 13 illustrates the response of the current follower in a dummy cell, which is the vector sum of the faradaic and charging current versus time.
Figure 14:
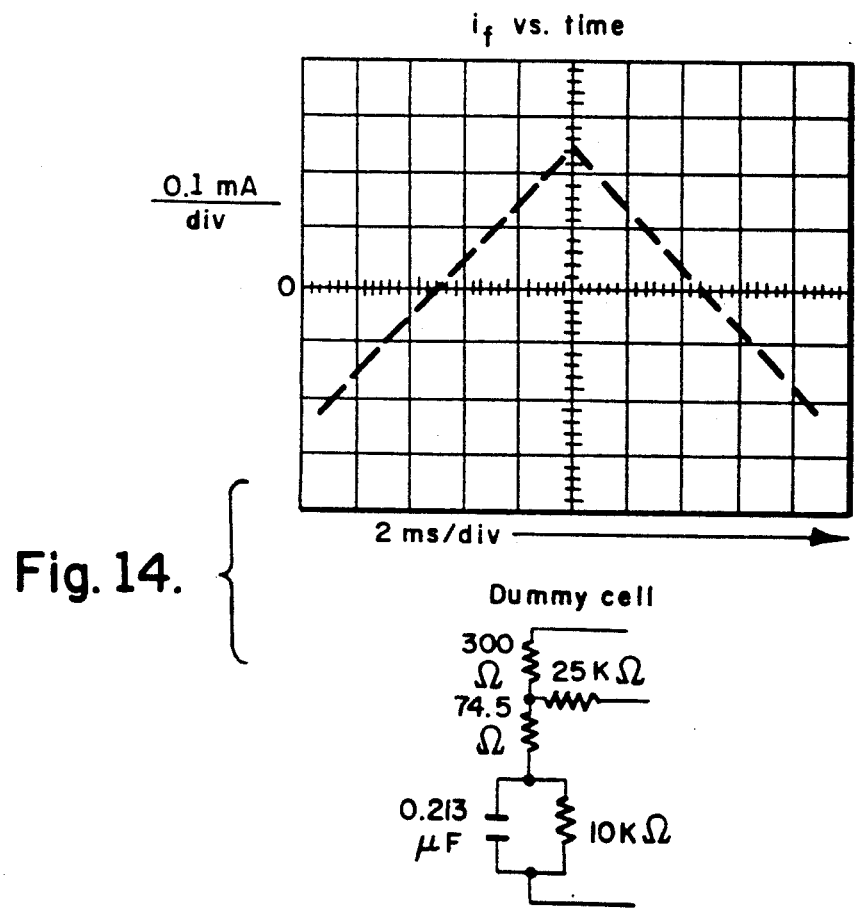
FIG. 14 illustrates the response at the summing amplifier in a dummy cell.

FIGS. 13 and 14 show the effects of charging current correction in the dummy cell shown beneath the figures. FIG. 13 is the response of the current follower which is the vector sum of the faradaic and charging current versus time. FIG. 14 is the response at the summing amplifier. The "dashed current" response in FIG. 13 is the result of intervals where the ramp potential is held constant. The "dashed current" response in FIG. 14 is due to the summing of currents at the summing amplifier. For instance, there is no charging current at the time the ramp potential is held constant. However, sample/hold 24 (shown in FIG. 2) is still summing the correction current into the summing amplifier. While the input signal is ramping, the output of the summing amplifier is:

$$-(i_f + i_c) - (-i_c) = -i_f \quad \text{(Eq. 15)}$$

At the time the ramp potential is held constant, the output of the summing amplifier is:

$$-(i_f) - (-i_c) = -i_f + i_c \quad \text{(Eq. 16)}$$

Thus, the "dashed current" response in FIG. 14.

The number of times the ramp potential was held constant is approximately 15 times per period. This was adequate to completely compensate for charging current as shown in FIG. 14.

The expected charging current is:

$$(0.213 \ \mu F)(543.5 \ V/s) = 0.116 \ mA \quad \text{(Eq. 17)}$$

and is shown as one-half the current drop when the ramp signal changes direction. Experiments confirm the calculated amount of 0.116 mA in Equation 17.

Electrochemical Cell Experiments

The digital difference technique of charging current correction not only corrects for charging current, but also subtracts an unknown amount of current due to faradaic processes whose rate is determined by electrode surface processes, and not by transport control involving solution speeds. Therefore, the change in current that takes place as a result of a hold in the ramp potential is due to not only charging current, but also to the change in surface faradaic current. The charging current will immediately drop to zero when the ramp potential is held constant (if there is compensation of the ohmic potential). However, surface faradaic current decreases slower than the charging current; consequently, charging current correction will be complete, and correction of electrolytic current will be incomplete by an unknown amount.

Figure 15:
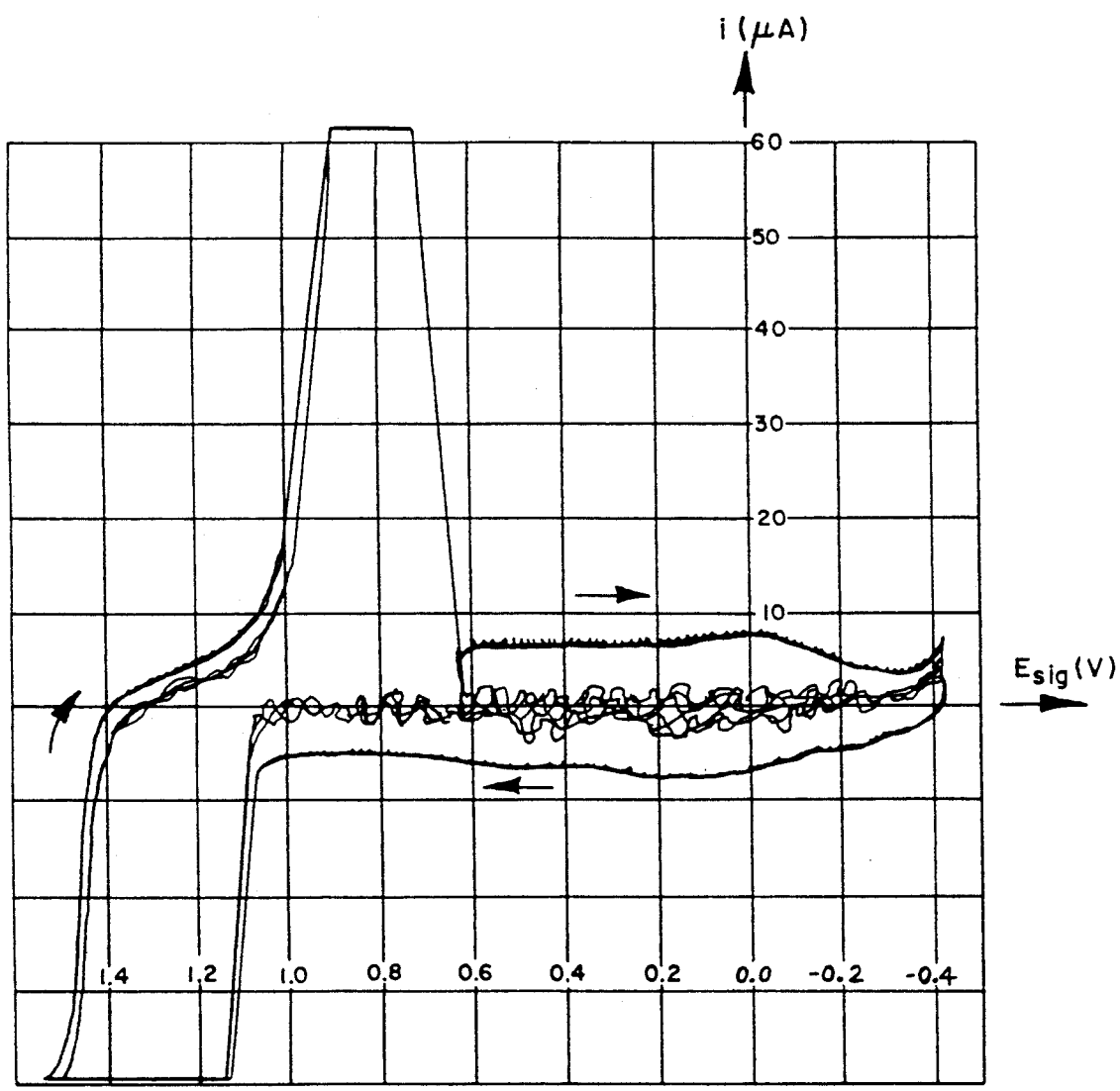
FIG. 15 illustrates charging current correction of 0.2M $H_2SO_4$ on a Au electrode.

Charging current correction of 0.2M $H_2SO_4$ on a Au rotating disk electrode is shown in FIG. 15. The scan rate is 0.640 V/s and the electrode surface area is 0.07116 $cm^2$. The electrode rotational speed is 1600 rpm. The upper potential limit is +1.533 V and the lower limit is −0.434 V. The circuit used in this experiment is shown in FIG. 2 with switch $S_3$ closed; the clock diagram is shown in FIG. 12 and the timing circuitry in FIG. 11. The component values are given in Table 5. The outer curve is without correction of charging current and is the total current ($i_f + i_c$) versus $E_{sig}$. The inner curve is with charging current correction. There is about 3 $\mu$A of noise in the charging current correction curve; but this noise could be eliminated by better circuit layout.

The flat region of the i-E curve shown in FIG. 15 from −0.434 to +0.6 V is characteristic of an ideally polarized electrode. There is an average of 7 $\mu$A of charging current within this region. Since the double-layer capacitance is equal to the charging current divided by the scan rate, it is calculated to be approximately 10.9 $\mu$F.

The outer curve of FIG. 15 is actually two curves. One curve is the output of the current follower when there is no hold in the ramp signal and the other curve is the current follower output when the input signal is the waveform shown in FIG. 3. A slight separation of the superimposed curves is observed at approximately +1.0 to +1.1 V. This slight separation is most probably due to delay in recorder response when the ramp potential is held constant. Since there is no additional noise due to the presence of sample/hold 20 in the circuit, the noise must be due to the digital difference circuit.

Charging current correction continues on the forward scan (the scan going from negative potentials to positive potentials, or the arrow pointing to the left) shown in FIG. 15 up until about +1.06 V and oxidation of water takes place at a faster rate. During the reverse scan (the scan going from positive potentials to negative potentials), there is about 2 $\mu$A of difference between the curve without and with correction from +1.4 V to 1.0 V. This is more pronounced when the electrode starts to reach an ideally polarized state and diminishes as the reduction rate of "Au-O" to Au and H₂O increases.

For the remainder of the reverse scan shown in FIG. 15, the charging current correction curve superimposes on the curve without correction during the decrease in rate of reduction of "Au-O" to Au. Charging current correction takes place immediately upon onset of an ideally polarized electrode.

Figure 16:
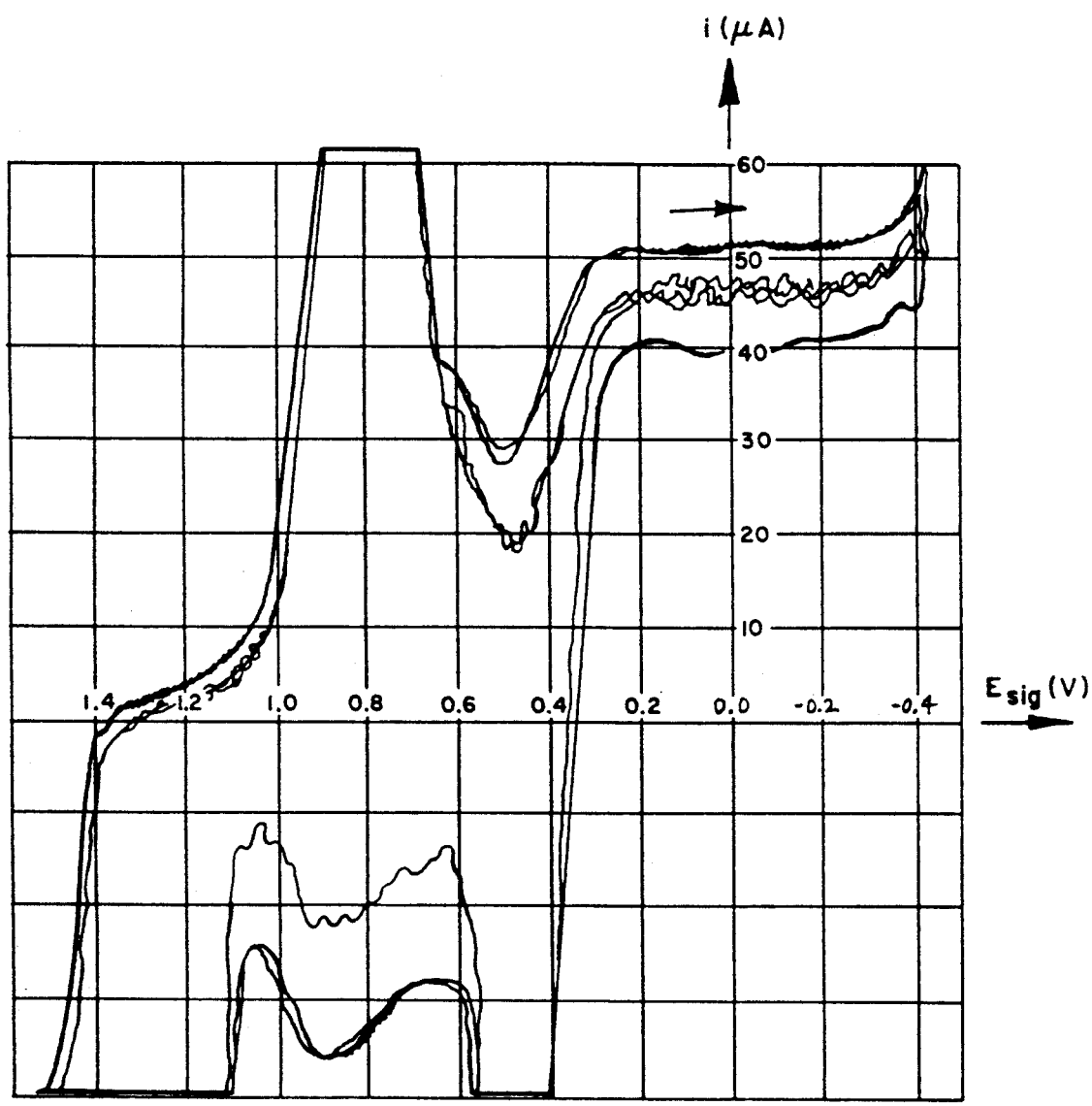
FIG. 16 shows charging current correction at a silver coated electrode.

FIG. 16 shows charging current correction at a silver coated gold RDE electrode (electrolyte/analyte are 0.2M $H_2SO_4$/0.61 mM $AgNO_3$, respectively). The electrode surface area is 0.07116 $cm^2$ and the rotational speed of the electrode is 1600 rpm. The scan rate is 0.640 V/s. The upper potential limit is +1.533 V and the lower limit is −0.434 V. The circuit used in this experiment is shown in FIG. 2 with switch $S_3$ closed; the clock diagram is shown in FIG. 12; the timing circuit is shown in FIG. 11 and the component values are given in Table 5. Charging current correction yields a limiting current of 46 μA which corresponds to a diffusion coefficient of $1.69 \times 10^{-5}$ $cm^2/s$. This agrees with the value found in the literature, $1.69 \times 10^{-5} cm^2/s$. See, e.g., Koltoff, I. M., Lingaine, J. J., Polarography, Vol. 1 at 28 (2d ed. 1952). Charging current is about 6 μA in the region of limiting current. The double-layer capacitance is calculated to be 9.4 μF. This is about 1 μF less than that which was observed in the electrolyte at the same signal input as shown in FIG. 15.

Charging current correction does not appear to be operating properly during the time of the onset of Ag° deposition. In other words, the forward scan (from negative to positive potentials) does not trace upon the reverse scan between the potentials of +0.30 to +0.46 V. This is due to underpotential deposition of Ag°. The scan rate is so rapid that the electrode does not become completely covered with Ag° before the limiting current region of the wave begins. Under slow scan conditions, the forward and reverse curves superimpose.

Figure 17:
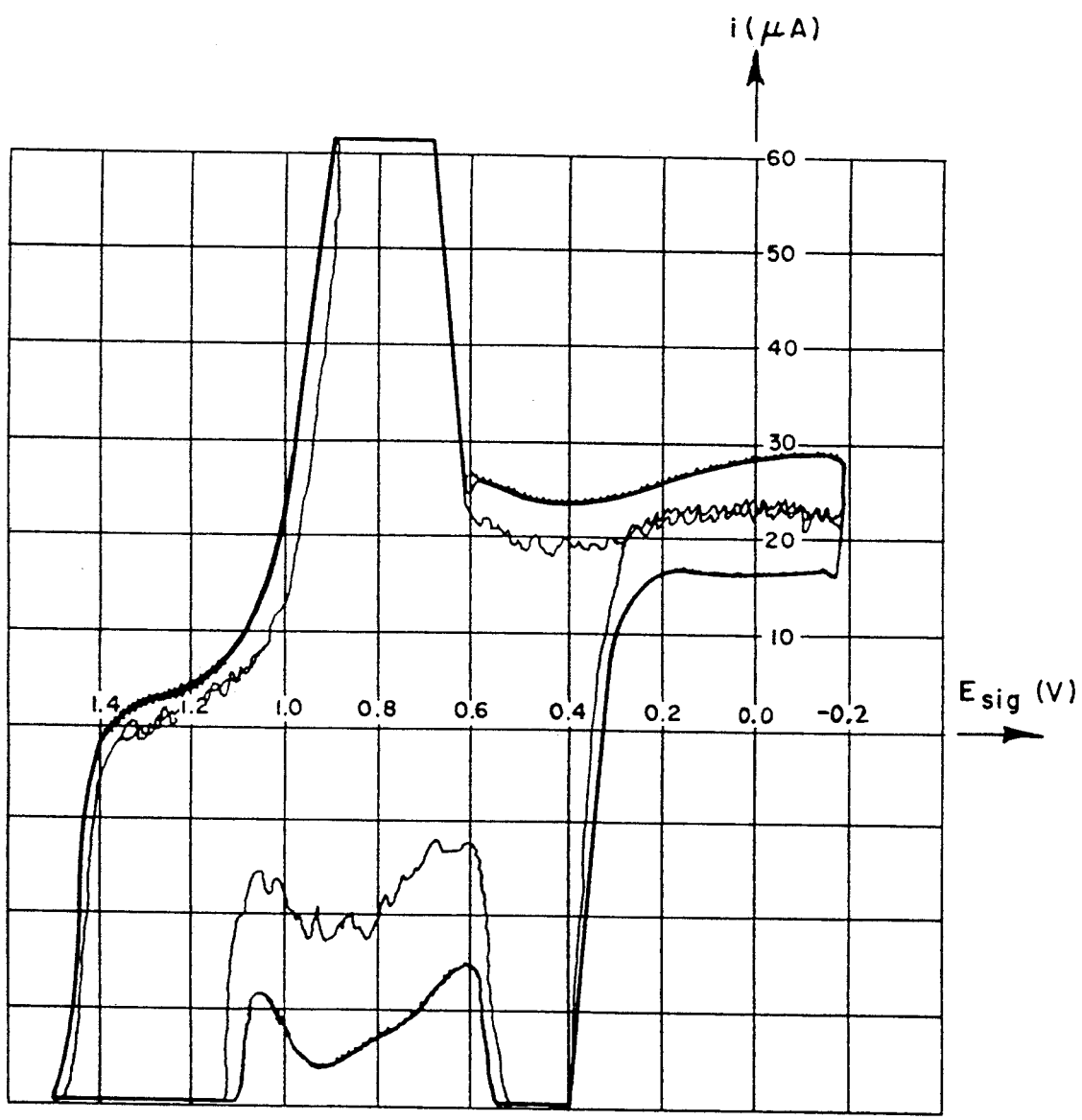
FIG. 17 illustrates results under the same experimental conditions of FIG. 16, but at a slower electrode rotation rate of 400 rpm.

FIG. 17 illustrates results under the same experimental conditions of FIG. 16, but at a slower rotation rate of 400 rpm. Although correction is almost completely masked by electrolyte reactions, the limiting current region shows correction and the limiting current is the expected value.

While the method and form of apparatus herein described constitute preferred embodiments of this invention, it is to be understood that the invention is not limited to this precise method or form of apparatus, and that changes may be made therein without departing from the scope of the invention; which is defined in the appended claims.

What is claimed is:

1. In an electrochemical cell having a reference electrode and, a working electrode and also having a time-varying potential difference applied between said electrodes, a method of measuring faradaic current at said working electrode, comprising interrupting said time-varying potential difference and temporarily applying a constant potential difference across said electrodes and measuring a current at said working electrode while said constant potential difference is applied, wherein said measured current is the faradaic current at said working electrode.

2. In an electrochemical cell having a reference electrode and a working electrode, a method of measuring charging current at said working electrode, comprising:
   measuring a first current at said working electrode while a time-varying potential difference is applied between said working electrode and said reference electrode;
   measuring a second current at said working electrode while a constant (non-time varying) potential difference is applied between said working electrode and said reference electrode, wherein said second current is the faradaic current at said working electrode; and
   measuring a difference between said first current and said second current, wherein said difference represents the charging current at said working electrode.

3. In an electrochemical cell having a counter electrode, a reference electrode, and a working electrode, a method of compensating for charging current at said working electrode, comprising:
   a. applying a time-varying potential difference between said working electrode and said reference electrode;
   b. measuring a first current at said working electrode while said time-varying potential difference is being applied, wherein said first current includes a faradaic current component and a charging current component;
   c. storing a first signal proportional to said first current in a first memory means;
   d. applying a constant, non-time-varying potential difference between said working electrode and said reference electrode;
   e. measuring a second current at said working electrode while said constant, non-time-varying potential difference is being applied, wherein said second current is said faradaic current component at an instant when said constant, non-time-varying potential difference is applied;
   f. determining a second signal proportional to said second current;
   g. determining a difference signal between said first and second signals;
   h. scaling said difference signal in magnitude and sign and summing said difference signal with said time-varying potential difference to produce a third signal, wherein said third signal is proportional to said charging current component; and,
   i. repeating steps a. through h. within preselected time intervals.

4. A method as recited in claim 3 wherein said first, second and third signals are voltages.

5. A method as recited in claim 3 wherein said time-varying potential difference is applied in repetitive cycles to said electrochemical cell and said non-time-varying potential difference is repetitively applied for a time period in the range of 1% to 25% of the time for each said cycle.

6. In an electrochemical cell having a reference electrode and a working electrode, an apparatus for measuring faradaic current at said working electrode, comprising:
   means for applying a time-varying potential difference between said working electrode and said reference electrode; and
   means for temporarily interrupting said application of said time-varying potential difference by temporarily applying a constant current across said working electrode and said reference electrode; and,
   means for measuring current at said working electrode while said constant potential difference is applied, where said measured current is the faradaic current at the working electrode.

7. In an electrochemical cell having a reference electrode and a working electrode, an apparatus for measuring charging current at said working electrode, comprising:

means for measuring a first current at said working electrode while a time-varying potential difference is applied between said working electrode and said reference electrode;

means for measuring a second current at said working electrode while a constant (non-time varying) potential difference is applied between said working electrode and said reference electrode, wherein said second current is the faradaic current at said working electrode; and means for measuring a difference between said first current and said second current, wherein said difference represents the faradaic current at said working electrode.

8. In an electrochemical cell having a counter electrode, a reference electrode, and a working electrode, an apparatus for compensating for charging current at said working electrode, comprising:

a. means for applying a time-varying potential difference between said working electrode and said reference electrode;

b. means for measuring a first current at said working electrode while said time-varying potential difference is being applied, wherein said first current includes a faradaic current component and a charging current component;

c. means for storing a first signal proportional to said first current in a first memory means;

d. means for applying a constant, non-time-varying potential difference between said working electrode and said reference electrode;

e. means for measuring a second current at said working electrode while said constant, non-time-varying potential difference is being applied, wherein said second current is said faradaic current component at an instant when said constant, non-time-varying potential difference is applied;

f. means for determining a second signal proportional to said second current;

g. means for determining a difference signal between said first and second signals;

h. means for scaling said difference signal in magnitude and sign and summing said difference with said time-varying potential difference to produce a third signal, wherein said third signal is proportional to said charging current component; and, i. means for repeating steps a. through h. within preselected time intervals.

9. Apparatus as recited in claim 8 wherein said first, second and third signals are voltages.

* * * * *